US012403122B2

(12) United States Patent
Lines (10) Patent No.: US 12,403,122 B2
(45) Date of Patent: Sep. 2, 2025

(54) METHOD FOR TREATING AMYOTROPHIC LATERAL SCLEROSIS USING QUERCETIN-CONTAINING COMPOSITIONS

(71) Applicant: Quercis Pharma AG, Zug (CH)

(72) Inventor: Thomas Christian Lines, Oberwil-Lieli (CH)

(73) Assignee: QUERCIS PHARMA AG, Zug (CH)

( * ) Notice: Subject to any disclaimer, the term of this patent is extended or adjusted under 35 U.S.C. 154(b) by 0 days.

(21) Appl. No.: 17/664,184

(22) Filed: May 19, 2022

(65) Prior Publication Data

US 2022/0370401 A1   Nov. 24, 2022

Related U.S. Application Data (60) Provisional application No. 63/190,697, filed on May 19, 2021.

(51) Int. Cl.
| | | |
|---|---|---|
| *A61K 31/352* | (2006.01) | |
| *A61K 31/375* | (2006.01) | |
| *A61K 31/404* | (2006.01) | |
| *A61K 31/455* | (2006.01) | |
| *A61K 31/519* | (2006.01) | |
| *A61P 21/00* | (2006.01) | |
| *A61P 25/28* | (2006.01) | |

(52) U.S. Cl.
CPC .......... *A61K 31/352* (2013.01); *A61K 31/375* (2013.01); *A61K 31/404* (2013.01); *A61K 31/455* (2013.01); *A61K 31/519* (2013.01); *A61P 21/00* (2018.01); *A61P 25/28* (2018.01)

(58) Field of Classification Search
CPC .. A61K 31/352; A61K 31/375; A61K 31/404; A61P 25/28
See application file for complete search history.

(56) References Cited

U.S. PATENT DOCUMENTS

| | | | |
|---|---|---|---|
| 7,745,486 B2 | 6/2010 | Lines | |
| 8,440,704 B2 * | 5/2013 | Lines | A61P 3/04 |
| | | | 514/474 |
| 8,680,053 B2 | 3/2014 | Lines | |
| 10,391,096 B2 | 8/2019 | Lines | |
| 2006/0276393 A1 | 12/2006 | Milburn et al. | |
| 2007/0248590 A1 | 10/2007 | Milne et al. | |
| 2008/0032987 A1 | 2/2008 | Lines | |
| 2011/0224290 A1 | 9/2011 | Estrela Ariquel et al. | |
| 2013/0028864 A1 | 1/2013 | Theoharides | |
| 2013/0095095 A1 | 4/2013 | Lines | |
| 2013/0129680 A1 | 5/2013 | Lines | |
| 2014/0350129 A1 | 11/2014 | Sikora et al. | |
| 2015/0366838 A1 | 12/2015 | Lines | |
| 2016/0263224 A1* | 9/2016 | Brittain | A61K 31/426 |
| 2016/0287591 A1 | 10/2016 | Lorence et al. | |
| 2020/0171064 A1 | 6/2020 | Zwicker et al. | |
| 2022/0000835 A1 | 1/2022 | Lines | |

FOREIGN PATENT DOCUMENTS

| | | | | |
|---|---|---|---|---|
| CN | 1895264 | A | 1/2007 | |
| CN | 100581552 | C | 1/2010 | |
| DE | 102006036307 | A1 | 2/2008 | |
| WO | 2001041751 | A2 | 6/2001 | |
| WO | 2003007846 | A1 | 1/2003 | |
| WO | 2006076681 | A2 | 7/2006 | |
| WO | 2006084142 | A2 | 8/2006 | |
| WO | 2014164285 | A2 | 10/2014 | |
| WO | 2014175253 | A1 | 10/2014 | |
| WO | 2015125137 | A1 | 8/2015 | |
| WO | 2015196036 | A1 | 12/2015 | |
| WO | WO-2005117924 | A1 * | 12/2015 | ........... A61K 31/355 |
| WO | 2018140858 | A1 | 8/2018 | |
| WO | 2018170457 | A1 | 9/2018 | |
| WO | 2020112828 | A1 | 6/2020 | |
| WO | WO-2021034942 | A1 * | 2/2021 | ............ A23L 33/12 |
| WO | 2022020659 | A1 | 1/2022 | |
| WO | 2022243942 | A1 | 11/2022 | |
| WO | 2023214391 | A1 | 11/2023 | |

OTHER PUBLICATIONS

Abnormal Upregulation of GPR17 Receptor Contributes to Oligodendrocyte Dysfunction in SOD1 G93A Mice, Int. J. Mol. Sci. 2020, 21, 2395 (Year: 2020).*
Drug Label of Zafirlukast (Year: 2011).*
The orphan receptor GPR17 identified as a new dual uracil nucleotides/cysteinyl-leukotrienes receptor The EMBO Journal (2006) 25, 4615-4627 (Year: 2006).*
Concentration-Dependent Noncysteinyl Leukotriene Type 1 Receptor-Mediated Inhibitory Activity of Leukotriene Receptor Antagonists J Immunol 2010, 184 (4), 2219-2225 (Year: 2010).*
K. Magalingam et al. Protective effects of quercetin glycosides, rutin, and isoquercetrin against 6-hydroxydopamine (6-OHDA)-induced neurotoxicity in rat pheochromocytoma (PC-12) cells. Int J Immunopathol Pharmacol. Mar. 2016;29(1):30-9. doi: 10.1177/0394632015613039. (Year: 2016).*
Zafirlukast Drug Label (Accolate) (Year: 2011).*
Y. Shen et al. Front. Physiol. 2020, 11:988. doi: 10.3389/fphys.2020.00988. (Year: 2020).*

(Continued)

*Primary Examiner* — James H Alstrum-Acevedo
*Assistant Examiner* — Manahil Mirghani Ali Abdalhameed
(74) *Attorney, Agent, or Firm* — DLA Piper LLP (US)

(57) ABSTRACT

Compositions and methods for treating amyotrophic lateral sclerosis. A method of treating amyotrophic lateral sclerosis comprising administering to a subject in need thereof an effective amount of quercetin, vitamin B3, vitamin C, zafirlukast and optionally folic acid. Also disclosed are methods of reducing, slowing or abating the progression of amyotrophic lateral sclerosis or a symptom thereof, comprising administering to a subject in need thereof an effective amount of quercetin, vitamin B3, vitamin C, zafirlukast and optionally folic acid.

13 Claims, 3 Drawing Sheets

(56) References Cited

OTHER PUBLICATIONS

L. Wang, et al. J Immunol 1 2011; 187 (5): 2336-2345. https://doi.org/10.4049/jimmunol.1100333. (Year: 2011).*

Bhatia et al. "Quercetin and Baicalein Act as Potent Antiamyloidogenic and Fibril Destabilizing Agents for SOD1 Fibrils" 2020, ACS Chemical Neuroscience, 11:1129-1138.

Crespy et al. "Quercetin, but not Its Glycosides, Is Absorbed from the Rat Stomach" 2002, J. Agricultural and Food Chemistry 50:618-621.

Curran et al. "Western New England University and Quercis Pharma Sign Exclusive Worldwide License Agreements" Quercis Pharma AG, News Release, May 19, 2021 (4 pages).

Fayez et al. "Neuroprotective effects of zafirlukast, piracetam and their combination on L-Methionine-induced vascular dementia in rats" 2019, Fundamental Clinical Pharmacology, 33:634-648.

Hermann et al. "Homocystein und B-Vitamine im Fokusvon Gefaeß- und neurodegenerativen Erkrankungen" Jun. 2011, Ernaehrung Und Medizin, Hippokrates Verlat Ins MVS Medizinverlage Stuttgart Gmgh & Co. KG 26:62-74.

International Search Report and Written Opinion for Application No. PCT/IB2022/054707 mailed Aug. 24, 2022.

Kalonia et al. "Protective Effect of Montelukast Against Quinolinic Acid/Malonic Acid Induced Neurotoxicity: Possible Behavioral, Biochemical, Mitochondrial and Tumor Necrosis Factor- α level Alterations in Rats" 2010, Neuroscience, 171:284-299.

Kuraszkiewicz et al. "Potential Preventive Strategies for Amyotrophic Lateral Sclerosis" May 26, 2020, Frontiers in Neuroscience, 14(428):1-11.

Middleton et al. "The Effects of Plant Flavonoids on Mammalian Cells: Implications for Inflammation, Heart Disease, and Cancer" Jan. 1, 2000, Pharmacological Reviews, American Society for Pharmacology and Experimental Therapeutics, United States 52(4):673-751, ISSN: 0031-6997, XP008047405.

Rakel "Integrative Medicine Second Ed." 2007, Botanical supplements Elsevier Saunders, 313-316.

Wang et al. "Antiasthmatic Drugs Targeting the Cysteinyl Leukotriene Receptor 1 Alleviate Central Nervous System Inflammatory Cell Infiltration and Pathogenesis of Experimental Autoimmune Encephalomyelitis" 2011, J. Immunol, 187:2336-2345.

Invitation to Pay Additional Fees for PCT/IB2023/054726 dated Jul. 18, 2023.

Faes et al. "Red blood cells modulate structure and dynamics of venous clot formation in sickle cell disease" Jun. 6, 2019, Blood 133(23):2529-2541.

Kato "Sickle cells and sickle trait in thrombosis" 2019, Blood 133(3):2463.

Back et al. "Anti-Inflammatory Therapies for Atherosclerosis" Oct. 2, 2015, Nature Reviews Cardiology 12:199-211.

Klotz "The Pharmacological Profile and Clinical Use of Mesalazine (5-Aminosalicylic Acid)" Feb. 2012, Arzneimittelforschung, 62:53-58.

Riccioni et al. "Antileukotriene Drugs: Clinical Application, Effectiveness and Safety" Aug. 1, 2007, Current Medicinal Chemistry 14(18):1966-1977.

Said et al. "The Anti-inflammatory Effect of Montelukast, a Cysteinyl Leukotriene Receptor-1 Antagonist, Against Estradiol-Induced Nonbacterial Inflammation in the Rat Prostate" Dec. 1, 2016, Naunyn-Schmiedeberg's Archives of Pharmacology 390(2):197-205.

Braga et al. "Drugs that inhibit TMEM16 proteins block SARS-COV-2 spike-induced syncytia" Jun. 1, 2021, Nature 594(7861):1-43.

Holbrook et al. "Zafirlukast is a broad-spectrum thiol isomerase inhibitor that inhibits thrombosis without altering bleeding times" 2021, British Pharma. Society 178:550-563.

Invitation to Pay Additional Fees for PCT/2023/083669 dated Apr. 2, 2024, 3 Pages.

Carrera-Julia et al. "Antioxidant alternatives in the treatment of amyotrophic lateral sclerosis: a comprehensive review" Feb. 6, 2020, Frontiers in Physiology, vol. 11:1-30.

European Examination Report for EP Application No. 22727463.6 dated Jan. 28, 2025.

Gelzinis et al. "Targeting Thiol Isomerase Activity with Zafirlukast to Treat Ovarian Cancer from the Bench to Clinic" Apr. 12, 2023, The FASEB Journal, vol. 37(5):1-14.

International Search Report and Written Opinion for application No. PCT/IB2023/054726 dated Sep. 8, 2023.

Ip et al. "Quercitrin and quercetin 3-Beta-D-glucoside as chemical chaperones for the A4V SOD1 ALS-causing mutant" May 5, 2017, Protein Engineering, Design and Selection, vol. 30(6):431-440.

* cited by examiner

FIG. 3

METHOD FOR TREATING AMYOTROPHIC LATERAL SCLEROSIS USING QUERCETIN-CONTAINING COMPOSITIONS

CROSS REFERENCE TO RELATED APPLICATIONS

This application claims priority from U.S. Provisional Patent Application No. 63/190,697, filed May 19, 2021. The contents of this application are incorporated herein by reference in its entirety for all purposes.

SUMMARY

The present disclosure relates to a method of treating amyotrophic lateral sclerosis (ALS), the method comprising administering to subject in need thereof an effective amount of quercetin, vitamin B3, vitamin C, zafirlukast and optionally folic acid.

BRIEF DESCRIPTION OF THE DRAWINGS

The accompanying drawings, which are incorporated in and form a part of the specification, illustrate the embodiments of the invention and together with the written description, serve to explain the principles, characteristics, and features of the invention. In the drawings.

DEFINITIONS

As used herein, "amyotrophic lateral sclerosis" or "ALS" refers to motor neuron disorders such as Primary Lateral Sclerosis (PLS), Progressive Muscular Atrophy (PMA), Pseudobulbar Palsy and Progressive Bulbar Palsy (PBP), as well as to Fronto Temporal Dementia (FTD).

As used herein, "quercetin" refers to both quercetin aglycone and quercetin derivatives, e.g., quercetin-3-O-glucoside (also known as "isoquercetin", and referred to herein as "IsoQ", "IsoQ or "Iso-Q"), quercetin-5-O-glucoside, quercetin-7-O-glucoside, quercetin-9-O-glucoside quercetin-3'-O-glucoside, quercetin-4'-O-glucoside, quercetin-3-O-rutinoside (also known as rutin), quercetin-3-O-[a-rhamnosyl-(1->2)-a-rhamnosyl-(1->6)]-I3-glucoside, quercetin-3-O-galactoside, quercetin-7-O-galactoside, quercetin-3-O-rhamnoside, quercetin-7-O-galactoside, quercetin-glycoside, 7-hydroxyflavone, and any pharmaceutically acceptable salts thereof "Quercetin" may also refer to isoquercetin or rutin or any constituent of rutin or isoquercetin, or metabolite or rutin or isoquercetin or quercetin, whether sulphated, glucuronidated or methylated form of rutin or quercetin, and any pharmaceutically acceptable salts thereof.

As used herein, "Vitamin B3" refers to vitamin B3 in its various forms, including, but not limited to niacinamide, nicotinic acid, nicotinamide, inositol hexaniacinate, or any combination thereof.

As used herein, "Vitamin C" refers to vitamin C including but not limited to L-ascorbic acid, D-ascorbic acid, or both and its salts (e.g., sodium ascorbate) or any combination thereof.

As used herein, "Folic acid" refers to a B vitamin including, but not limited to vitamin B9, folate, pteroylglutamic acid, and L-methyl folate, 5-MTHF (5-methyltetrahydrofolate) or any combination thereof.

As used herein, "thiol isomerases" which includes but is not limited to "extracellular thiol isomerases" and "vascular thiol isomerases", are multifunctional enzymes that influence protein structure via their oxidoreductase, isomerase, and chaperone activities. These enzymes localize at high concentrations in the endoplasmic reticulum of all eukaryotic cells where they serve an essential function in folding nascent proteins by mediating disulphide bond formation. However, thiol isomerases can escape endoplasmic retention and be secreted and localized on plasma membranes. Several thiol isomerases including but not limited to protein disulfide isomerase (PDI), ERp57, and ERp5 are secreted by and localize to the membranes of platelets and endothelial cells. These vascular thiol isomerases are released following vessel injury and are known to participate in thrombus formation. Vascular thiol isomerases also act as redox sensors. They respond to the local redox environment and influence S-nitrosylation of surface proteins on platelets and endothelial cells. In addition to their role in protein folding, thiol isomerases can modify allosteric disulphide bonds in both intracellular and extracellular proteins, thereby controlling protein function. The process of disulphide bond formation and cleavage is strictly regulated and responsive to redox conditions. PDI, the prototype of these thiol isomerases, has a molecular weight of 57,000 and includes 508 amino acids. Encoded by the P4HBgene, it is composed of four thioredoxin-like domains a-b-b'-a', where a and a' are catalytically active units with the CGHC motif in the active site and preceded by a signal sequence. "Thiol isomerases" include but are not limited to protein disulfide isomerase (PDI), PDIA2, PDIA3 (also known as glucose-regulated protein, 58-kD (GRP58)), PDIA4, PDIA5, PDIA6, PDIALT, PPIA, thioredoxin (TRX), AGR2, AGR3, CASQ1, CASQ2, DNAJC10, P4HB, TMX1, TMX2, TMX3, TMX4, TXNDC5, and TXNDC12 and the following endoplasmic reticulum resident proteins: ERp5, ERp27, ERp57, ERp72, ERp44, ERp46, ERp29.

As used herein, "thiol isomerase inhibitor compound" is an inhibitor of one or more of the thiol isomerases. Exemplary thiol isomerase inhibitor compounds include zafirlukast, montelukast, CGP-13501 (CAS Reg. No. 56189-68-5), CGP-7930 (CAS Reg. No. 57717-80-3), alosetron, balsalazide, benserazide, butaclamol, leva-dopa, mesalazine, oxcarbazepine, a pharmaceutically acceptable salt, prodrug, and/or solid-state form thereof. As inhibitors of one or more of the thiol isomerases, one or more of these compounds or a combination of two or more of these compounds can be used as an anti-thrombotic agent, and anticoagulant agent, an anti-inflammatory agent, an anti-viral agent, a chemotherapeutic or an anti-cancer agent, etc., or a combination thereof. Zafirlukast is a synthetic, selective peptide leukotriene receptor antagonist (LTRA), with the chemical name 4-(5-cyclopentyloxycarbonylamino-1-methylindol-3-ylmethyl)-3-methoxy-N-o-tolylsulfonylbenzamide. We have found zafirlukast to be a broad-spectrum thiol isomerase inhibitor that inhibits platelet function, thrombus formation and cancer cell growth. The synthesis and pharmaceutical forms of zafirlukast are further described in U.S. Pat. Nos. 4,859,692; 5,294,636; 5,319,097; 5,482,963; 5,583,152; 5,612,367; 6,143,775; 6,333,361; and 6,399,104, the contents of which are incorporated herein by reference in their entireties. Montelukast is a synthetic peptide leukotriene receptor antagonist (LTRA), with the chemical name [R-(E)]-1-[[[1-[3-[2-(7-chloro-2-quinolinyl)ethenyl] phenyl]-3-[2-(7-chloro-2-quinolinyl)ethenyl]phenyl]-3-[2-(1-hydroxy-1-methylethyl)phenyl]propyl]thio]methyl cyclo-propane acetic acid. The synthesis and pharmaceutical forms of montelukast and montelukast sodium are further described in U.S. Pat. No. 5,565,473, which is incorporated herein by reference in its entirety.

As used herein, the term "pharmaceutical agent" or "compound" refers to a chemical entity or biological product, or a combination of chemical entities or biological products, administered to a person to treat or prevent or control a disease or condition.

The term "active agent", as used herein, means a compound, element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound, crystalline forms, non-crystalline (i.e., amorphous) forms, and any polymorphs of the compound are included. All forms are contemplated herein regardless of the methods used to obtain them.

The term "pharmaceutically acceptable salt," as used herein, includes derivatives of the disclosed compounds in which the parent compound is modified by making inorganic and organic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are used, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)_n-COOH$ where n is 0-4, and the like. Lists of additional suitable salts may be found, e.g., in *Remington's Pharmaceutical Sciences,* 17th ed., Mack Publishing Company, Easton, Pa., p. 1418 (1985).

As used herein, the term "about" when immediately preceding a numerical value means a range of plus or minus 10% of that value, for example, "about 50" means 45 to 55, "about 25,000" means 22,500 to 27,500, etc., unless the context of the disclosure indicates otherwise, or is inconsistent with such an interpretation.

The term "dosage form", as used herein, means a unit of administration of an active agent. Examples of dosage forms include tablets, capsules, injections, suspensions, liquids, emulsions, creams, ointments, suppositories, inhalable forms, transdermal forms, and the like. An exemplary dosage form is a solid oral dosage form.

The term "pharmaceutical compositions", as used herein, are compositions comprising at least one active agent or a pharmaceutically acceptable salt thereof, and at least one other substance, such as a carrier. Pharmaceutical compositions meet the U.S. FDA's GMP (good manufacturing practice) standards for human or non-human drugs. The pharmaceutical compositions can be formulated into a dosage form.

The term "carrier", as used herein, applied to pharmaceutical compositions refers to a diluent, excipient, or vehicle with which an active agent is provided. The term "carrier", as used herein, applied to pharmaceutical compositions refers to a diluent, excipient, or vehicle with which an active agent is provided. Classes of carriers include, for example, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin, talc, and vegetable oils. Optional additional active agent may be included in a pharmaceutical composition, which do not substantially interfere with the activity of the active agent. The amount of carrier employed in conjunction with the compound is sufficient to provide a practical quantity of material for administration per unit dose of the active agent. Classes of carriers include, for example, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin, talc, and vegetable oils. Optional active agents may be included in a pharmaceutical composition, which do not substantially interfere with the activity of the active agent.

The term "patient" or "subject" as used herein, is a human or non-human animal in need of medical treatment. Medical treatment can include treatment, arresting or slowing or amelioration of an existing condition, such as a disease or disorder, prophylactic or preventative treatment or diagnostic treatment in patients with a family history of ALS (research has shown that in about 10% of patients with ALS, there is a clear family history for ALS, suggesting a strong genetic predisposition, and currently a pathogenic mutation can be found in more than half of these cases. On the other hand, apparently sporadic ALS is considered a complex trait for which heritability is estimated at 40-50%). In some embodiments the patient is a human patient.

As used herein, the terms "administer," "administering" or "administration" as used herein refer to directly administering a compound or a composition to a subject.

The term "providing", as used herein, means giving, administering, selling, distributing, transferring (for profit or not), manufacturing, compounding, or dispensing.

The term "providing a thiol isomerase inhibitor compound or pharmaceutically acceptable salt thereof with at least one additional therapeutic agent", as used herein, means an active agent or pharmaceutically acceptable salt thereof and the additional active agent(s) are provided simultaneously in a single dosage form, provided concomitantly in separate dosage forms, or provided in separate dosage forms for administration separated by some amount of time that is within the time in which both the active agent or pharmaceutically acceptable salt thereof and the at least one additional active agent are within the blood stream of a patient. The active agent or pharmaceutically acceptable salt thereof and the additional active agent need not be prescribed for a patient by the same medical care worker. The additional active agent or agents need not require a prescription. Administration of the active agent or pharmaceutically acceptable salt thereof or the at least one additional active agent can occur via any appropriate route, for example, oral tablets, oral capsules, oral liquids, inhalation, injection, suppositories or topical contact.

The term "treatment", as used herein, includes providing an active agent or pharmaceutically acceptable salt thereof, either as the only active agent or together with at least one additional active agent sufficient to: (a) prevent a disease or condition or a symptom of a disease or condition from occurring in a patient who may be predisposed to the disease or condition but has not yet been diagnosed as having it (in patients with a family history of ALS); (b) inhibiting the disease or condition, i.e. arresting or slowing its development (in some embodiments, after a diagnosis of ALS); and (c) relieving the disease or condition, i.e., causing regression of the disease or condition. "Treating" and "treatment" also means providing a therapeutically effective amount of an active agent or pharmaceutically acceptable salt thereof, as the only active agent or together with at least one additional active agent to a patient suffering from a disease or condition influenced by the activity of one or more active agents. "A disease or condition influenced by the activity of one or more active agents" means the one or more active agents is implicated in the disease or condition.

As used herein, the term "effective amount" refers to an amount that results in measurable inhibition of at least one symptom or parameter of a specific disorder or pathological process. As used herein the term "therapeutically effective amount" of compositions of the application is an amount, which confers a therapeutic effect on the treated subject, at a reasonable benefit/risk ratio applicable to any medical treatment. The therapeutic effect may be objective (that is, measurable by some test or marker) or subjective (that is, subject gives an indication of or feels an effect or physician observes a change).

The term "therapeutically effective amount" of an active agent, as used herein, means an amount effective, when administered to a patient, to provide a therapeutic benefit such as a prevention (in patients with a family history of ALS), slowing, inhibition, or an amelioration of symptoms, e.g., to prevent the activation of mast cells and prevent the formation of mast cell activated cytokines in a patient suffering from, ALS. A therapeutically effective amount may vary according to factors such as the health, age, and weight of the patient, and the ability of the compound to elicit a desired response in the patient. Dosage regimens may be adjusted to provide the optimum therapeutic response. A therapeutically effective amount is also one in which any toxic or detrimental effects (e.g., side effects) of the active agent are outweighed by the therapeutically beneficial effects.

The term "synergistic effect" as used herein, refers to an interaction or cooperation giving rise to a whole that is greater than the simple sum of its parts. As used herein, the effect of isoquercetin or quercetin and zafirlukast produces results that are greater than either quercetin or zafirlukast alone.

The term "preventing" may be taken to mean to prevent a specific disorder, disease or condition and/or prevent the reoccurrence of a specific disorder, disease or condition. In some embodiments, "preventing" may be taken to mean to prevent a specific disorder, disease or condition and/or prevent the reoccurrence of a specific disorder, disease or condition in a patient with a family history of ALS.

As used herein, the term "prognosis" means the probable course and outcome of a disease, especially of the chances of recovery.

As used herein the terms "treat", "treatment", "treated", or "treating" refer to both therapeutic treatment and prophylactic or preventative measures (in the case of patients with a family history of ALS), wherein the object is to protect against (partially or wholly) or slow down (for example, lessen or postpone the onset of) an undesired physiological condition, disorder or disease, or to obtain beneficial or desired clinical results such as partial or total restoration or inhibition in decline of a parameter, value, function or result that had or would become abnormal. For the purposes of this application, beneficial or desired clinical results include, but are not limited to, alleviation of symptoms; diminishment of the extent or vigor or rate of development of the condition, disorder or disease; stabilization (that is, not worsening) of the state of the condition, disorder or disease; delay in onset or slowing of the progression of the condition, disorder or disease; amelioration of the condition, disorder or disease state; and remission or recurrence (whether partial or total), whether or not it translates to immediate lessening of actual clinical symptoms, or enhancement or improvement of the condition, disorder or disease; preventing spread of the condition, disorder or disease state. Treatment seeks to elicit a clinically significant response without excessive levels of side effects. The term "unit dosage form" refers to physically discrete units suitable as a unitary dosage for human subjects and other animals, each unit containing a predetermined quantity of active material calculated to produce the desired therapeutic effect, in association with a suitable pharmaceutical excipient.

The terms "improving," "enhancing," "treating," and "lowering" refer to the administration of an effective amount of a composition of the invention to a subject, who needs to improve one or more of the above-mentioned conditions or has one or more of the just-mentioned disorders, or a symptom or a predisposition of one of more of the disorders or conditions, with the purpose to improve one or more of these conditions, or to prevent, cure, alleviate, relieve, remedy, or ameliorate one or more of these disorders, or the symptoms or the predispositions of one or more of them.

The term "administration" covers oral or parenteral delivery to a subject a composition of the invention in any suitable form, e.g., food product, beverage, tablet, capsule, suspension, and solution.

The term "parenteral" refers to subcutaneous, intracutaneous, intravenous, intramuscular, intraarticular, intraarterial, intra-synovial, intrasternal, intranasal, intrathecal, intralesional, and intracranial injection, as well as various infusion techniques.

An "effective amount" refers to a dose of the composition that is sufficient to provide a physical benefit (e.g., reducing fatigue brought on by the disease and/or improving endurance) or a therapeutic benefit (e.g., slowing ALS disease progression). Both in vivo and in vitro studies can be conducted to determine optimal administration routes and doses.

The term "disease" as used herein is intended to be generally synonymous, and is used interchangeably with, the terms "disorder," "dysfunction," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a medical condition or disorder described in the present disclosure. Such administration encompasses co-administration of these therapeutic agents in a substantially simultaneous manner, such as in a single capsule, or dosage presentation, having a fixed ratio of active ingredients or in multiple, separate capsules for each active ingredient. In addition, such administration also encompasses use of each type of therapeutic agent in a sequential manner in the same patient, with delivery of the individual therapeutics separated by 1-24 hours, 1-7 days, or 1 or more weeks. In either case, the treatment regimen will provide beneficial effects of the drug combination in treating the conditions or disorders described herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

DETAILED DESCRIPTION

Various methods are described herein for the treatment of amyotrophic lateral sclerosis (ALS) or a related disorder selected from Primary Lateral Sclerosis (PLS), Progressive Muscular Atrophy (PMA), Pseudobulbar Paralysis and Progressive Bulbar Paralysis (PBP), multiple sclerosis (MS), Frontotemporal Dementia (FTD) and Huntington's disease. The methods include administration of at least one pharmaceutical composition to the subject. The treatment can reduce or eliminate the symptoms of ALS. The treatment can halt further progression of the symptoms of ALS (e.g., lung dysfunction and/or the inability to fully expand the lungs). The treatment can slow further progression of the symptoms of ALS (e.g., lung dysfunction and/or the inability to fully expand the lungs). Thiol isomerase inhibitors and particularly PDI inhibitors can suppress or stop the activation of mast cells and prevent or inhibit the activation of mast cells, reduce mast cell overactivity, can preserve mitochondrial function and protect neurons from degeneration as well as prevent or reduce the loss of lung function and/or the inability to fully expand the lungs as seen in ALS.

In one embodiment, the present invention describes a method of treating amyotrophic lateral sclerosis (ALS), the method comprising administering to a subject in need thereof an effective amount of quercetin, vitamin B3, vitamin C, zafirlukast and optionally folic acid. The composition of this invention can be in various forms. In some embodiments, quercetin, vitamin B3, and vitamin C and optionally folic acid, are administered in a single formulation and zafirlukast and optionally folic acid, are administered separately. In some embodiments, quercetin, vitamin B3, vitamin C, zafirlukast, and optionally folic acid, are administered separately. In some embodiments, quercetin, vitamin B3, vitamin C, zafirulkast and optionally folic acid, are administered in a single formulation. In some embodiments, quercetin, vitamin B3, vitamin C, zafirulkast and optionally folic acid, may be administered in one or more formulations, wherein any one of quercetin, vitamin B3, vitamin C, zafirlukast and optionally folic acid, may be administered in combination or alone.

This invention is based, at least in part, on the unexpected findings that a composition comprising quercetin, vitamin B3, vitamin C, zafirlukast and optionally folic acid, as active ingredients exhibit synergistic effects in treating patients with ALS compared to treatment with either isoquercetin or quercetin or zafirlukast alone. Zafirlukast, a broad-spectrum thiol isomerase inhibitor, and isoquercetin or quercetin act largely on different thiol isomerases. Thiol isomerases, in general, can damage the spinal cord through mast cell activation, aberrant mast cell activity, and mitochondrial dysfunction, which lead to neuroinflammation, microglia activation and damage, and cell death. Zafirlukast protects motor neurons against neuroinflammation, which is one of the etiological causes of nerve degeneration in ALS. Zafirlukast may also inhibit aberrant mast cells activity which in turn may inhibit the loss of lung function and/or the inability of patients to fully inflate lungs that is observed in patients with ALS. Quercetin and isoquercetin are known to protect against mitochondrial dysfunction and preserve mitochondrial biogenesis, another one of the etiological causes of nerve degeneration in ALS. Quercetin and isoquercetin may also inhibit aberrant mast cells activity which in turn may inhibit the loss of lung function and/or the inability of patients to fully inflate lungs that is observed in patients with ALS albeit by inhibiting different thiol isomerases than zafirlukast. Moreover, the inventors have observed the surprising result that these compounds, at low doses, act synergistically to efficiently protect motor units. Moreover, the composition comprising quercetin, vitamin B3, vitamin C, zafirlukast and optionally folic acid, as active ingredients therapies can delay the onset of paralysis in vivo and prolong survival in animal models of ALS. The composition comprising quercetin, vitamin B3, vitamin C, zafirlukast and optionally folic acid, represents a surprising and substantial improvement in the treatment of ALS subjects.

Pharmaceutical Compositions

In some embodiments, a method of treating amyotrophic lateral sclerosis (ALS), the method comprising administering to a subject in need thereof an effective amount of quercetin, vitamin B3, vitamin C, a thiol isomerase inhibitor, and optionally folic acid, wherein the thiol isomerase inhibitor is zafirulkast, montelukast, CGP-13501, CGP-7930, alosetron, balsalazide, benserazide, butaclamol, leva-dopa, mesalazine, oxcarbazepine, a pharmaceutically acceptable salt, prodrug, and/or a solid state form thereof. In some embodiments, a method of treating ALS, the method comprising administering to a subject in need thereof an effective amount of quercetin, vitamin B3, vitamin C, zafirlukast and optionally folic acid.

In some embodiments, a method of treating ALS, the method comprising administering to a subject in need thereof an effective amount of quercetin, vitamin B3, vitamin C, zafirlukast, and optionally folic acid, wherein the composition includes about 250 mg to about 1000 mg of quercetin. In some embodiments, the composition includes about 20 µg to about 3 g of Vitamin B3. In some embodiments, the composition includes about 200 µg to about 3 g of Vitamin C. In some embodiments, the composition includes about 1000 µg to about 3000 µg of folic acid. In some embodiments, the composition includes about 5 mg to about 160 mg of zafirlukast. In some embodiments, the composition includes about 5 mg to about 320 mg, about 80 mg to about 160 mg, or about 5 mg to about 80 mg of zafirlukast.

The weight ratio between quercetin, vitamin B3, vitamin C, folic acid, and zafirlukast in a composition of the invention can be 1:0.02-1:0.2-2.5, or any ratio in between. For example, the weight ratio can be 1:0.04-0.5:0.3-2.0, 1:0.05-0.3:0.4-1.5, 1:0.05-0.2:0.5-1, and 1:0.1-0.2:0.5-1. Preferred ratios include about 1:0.02:1, about 1:0.04:1, about 1:0.08:1, about 1:0.05:1.5, and about 1:0.16:1. Typically, a subject can be administered, once or periodically per day, with the composition in an amount that provides 100 mg to 2 g (preferably, 250 mg to 1 g) of quercetin.

After digestion, quercetin derivatives are converted to quercetin aglycon and other active derivatives, which are absorbed in the body. The quantity of quercetin mentioned above refers to that of quercetin aglycon or the quercetin moiety of a quercetin derivative. Quercetin can be added to a composition either in a pure form or as an ingredient in a mixture (e.g., a plant extract). Examples of commercially available quercetin include QU995 (containing 99.5% quercetin) and QU985 (containing 98.5% quercetin) from Quercegen Pharmaceuticals LLC (Boston, Mass.). Examples of commercially available isoquercetin include ISQ950AN (greater than or equal to 95% isoquercetin) and ISQ995AN (containing 99.5% isoquercetin) from Quercis Pharma AG (Zug, Switzerland).

Compositions of this invention can be in various forms including but not limited to soft chews, capsules, tablets, and the like. For example, a composition may be a soft chew composition that includes quercetin, niacinamide, ascorbic acid, sodium ascorbate, sugar, corn syrup, sucralose, soy lecithin, corn starch, clycerin, palm oil, xylitol, carrageenan, FD&C Yellow #6, FD&C Yellow #5, and natural and/or artificial flavors. An exemplary serving of this soft chew composition (5.15 g) includes 250 mg of quercetin, 12.9 mg of vitamin B3 (i.e., niacinamide), and 382.8 mg vitamin C (i.e., L-ascorbic acid and sodium ascorbate). Folic acid may be provided in the soft chew or separately in an amount of about 1000 µg to about 3000 µg. Zafirlukast may be provided in the soft chew or separately in an amount of about 5 mg to about 320 mg, about 80 mg to about 160 mg, or about 5 mg to about 80 mg. A subject can take one to eight servings (e.g., 4 servings) of this soft chew composition daily. The amounts taken can vary depending on, for example, the disorder or condition to be treated and the physical states of the subject. Another exemplary composition of this soft chew includes 5.25 wt % of quercetin, 0.25 wt % of vitamin B3, and 7.81 wt % of vitamin C (i.e., L-ascorbic acid and sodium ascorbate).

Compositions of this invention can further contain one or more active ingredients, such as an isoflavone (e.g., genistein or genistin), curcumin, resveratrol, isoquercetin, luteolin, epigallocatechin gallate (EGCG), CoQ10, eicosapentaenoic acid (EPA), and docosahexaenoic acid (DHA). These active ingredients can be added to the composition either in a pure form or as a component in a mixture (e.g., an extract from a plant or an animal). A suitable daily dosage of each of these ingredients can vary depending on, for example, the disorder or condition to be treated and the physical states of the subjects. Exemplary daily dosages of some of these ingredients are: 20-2,500 mg (preferably 250-1,000 mg) of curcumin, 10-1,000 mg (preferably 100-500 mg) of resveratrol, 10-1,000 mg (preferably 100-250 mg) of isoquercetin, 50-1,000 mg (preferably 100-700 mg) of EGCG, 25-300 mg (preferably 50-100 mg) of genistin/genistein, 10-1,000 mg (preferably 100-200 mg) of luteolin, 50-1,000 mg (preferably 70-500 mg) of EPA, and 50-1,000 mg (preferably 80-700 mg) of DHA. Further, it can be sweetened, if necessary, by adding a sweetener such as sorbitol, maltitol, hydrogenated glucose syrup and hydrogenated starch hydrolyzate, high fructose corn syrup, cane sugar, beet sugar, pectin, and sucralose. The composition can also contain amino acids, fatty acids, proteins, fibers, minerals, a flavor enhancer, or a coloring agent. Exemplary amino acids include glycine, alanine, valine, leucine, isoleucine, proline, serine, threonine, cysteine, methionine, phenylalanine, tyrosine, tryptophan, aspartate, glutamate, histidine, lysine, arginine and their L- and D-configurations. Amino acids may be added to aid in digestion. Exemplary fatty acids include omega-3 fatty acids (e.g., linolenic acid), omega-6 fatty acids (e.g., linoleic acid), omega-9 fatty acids (e.g., oleic acid), sunflower oil, sunflower lecithin, soy oil, and soy lecithin. Amino acids may be added to aid in digestion. Exemplary proteins include plant proteins, such as soy proteins and chia seed proteins. Exemplary fibers include plant fibers, such as soy fibers and chia seed fibers. These ingredients can be added in the above-described composition either in a pure form or as a component in a mixture (e.g., an extract from a plant or an animal).

In some examples, pharmaceutical compositions can further comprise one or more exemplary fillers. Examples of exemplary fillers include cellulose and cellulose derivatives such as microcrystalline cellulose; starches such as dry starch, hydrolyzed starch, and starch derivatives such as corn starch; cyclodextrin; sugars such as powdered sugar and sugar alcohols such as lactose, mannitol, sucrose and sorbitol; inorganic fillers such as aluminum hydroxide gel, precipitated calcium carbonate, carbonate, magnesium aluminometasilicate, dibasic calcium phosphate; and sodium chloride, silicon dioxide, titanium dioxide, titanium oxide, dicalcium phosphate dihydrate, calcium sulfate, alumina, kaolin, talc, or combinations thereof. Fillers may be present in the composition from about 20 wt % to about 65 wt %, about 20 wt % to about 50 wt %, about 20 wt % to about 40 wt %, about 45 wt % to about 65 wt %, about 50 wt % to about 65 wt %, or about 55 wt % to about 65 wt % of the total weight of the composition, or any value between these ranges.

In some examples, pharmaceutical compositions further comprise one or more disintegrants. Examples of disintegrants include starches, alginic acid, crosslinked polymers such as crosslinked polyvinylpyrrolidone, croscarmellose sodium, potassium starch glycolate, sodium starch glycolate, clays, celluloses, starches, gums, or combinations thereof. Disintegrants may be present in the composition from about 1 wt % to about 10 wt %, about 1 wt % to about 9 wt %, about 1 wt % to about 8 wt %, about 1 wt % to about 7 wt %, about 1 wt % to about 6 wt %, or about 1 wt % to about 5 wt % of the total weight of the composition, or any value between these ranges.

In some examples, pharmaceutical compositions further comprise one or more binders, including but not limited to celluloses such as hydroxypropylcellulose, methyl cellulose, and hydroxypropylmethylcellulose; starches such as corn starch, pregelatinized starch, and hydroxypropyl starch; waxes and natural and synthetic gums such as acacia, tragacanth, sodium alginate; synthetic polymers such as polymethacrylates and polyvinylpyrrolidone; and povidone, dextrin, pullulane, agar, gelatin, tragacanth, macrogol, or combinations thereof. Binders may be present in the composition from about 0.5 wt % to about 5 wt %, about 0.5 wt % to about 4 wt %, about 0.5 wt % to about 3 wt %, about 0.5 wt % to about 2 wt %, or about 0.5 wt % to about 1 wt % of the total weight of the composition, or any value between these ranges.

In some examples, pharmaceutical compositions further comprise one or more wetting agents, including but not limited to oleic acid, glyceryl monostearate, sorbitan monooleate, sorbitan monolaurate, triethanolamine oleate, polyoxyethylene sorbitan mono-oleate, polyoxyethylene sorbitan monolaurate, sodium oleate, sodium lauryl sulfate, poloxamers, poloxamer 188, polyoxyethylene ethers, polyoxyethylene sorbitan fatty acid esters, polyoxyethylene fatty acid esters, polyethylene glycol fatty acid esters, polyoxyethylene hardened castor oil, polyoxyethylene alkyl ethers, polysorbates, cetyl alcohol, glycerol fatty acid esters (for example, triacetin, glycerol monostearate, etc.), polyoxymethylene stearate, sodium lauryl sulfate, sorbitan fatty acid esters, sucrose fatty acid esters, benzalkonium chloride, polyethoxylated castor oil, and combinations thereof. Wetting agents may be present in the composition from about 0.1 wt % to about 1 wt %, about 0.1 wt % to about 2 wt %, about 0.1 wt % to about 3 wt %, about 0.1 wt % to about 4 wt %, or about 0.1 wt % to about 5 wt % of the total weight of the composition, or any value between these ranges.

In some examples, pharmaceutical compositions further comprise one or more lubricants, including but not limited to stearic acid, magnesium stearate, calcium hydroxide, talc, corn starch, sodium stearyl fumarate, alkali-metal and alkaline earth metal salts, waxes, boric acid, sodium benzoate, sodium acetate, sodium chloride, leucine, polyethylene glycol (PEG), a methoxypolyethylene glycol, propylene glycol, sodium oleate, glyceryl behenate, glyceryl palmitostearate, glyceryl benzoate, magnesium lauryl sulfate, sodium lauryl sulfate, and combinations thereof. Lubricants may be present in the composition from about 0.1 wt % to about 5 wt %, about 0.1 wt % to about 4 wt %, about 0.1 wt % to about 3 wt %, about 0.1 wt % to about 2 wt %, or about 0.1 wt % to about 1 wt % of the total weight of the composition, or any value between these ranges.

In some examples, the pharmaceutical composition further comprises one or more glidants, including but not limited to colloidal silicon dioxide, talc, sodium lauryl sulfate, native starch, and combinations thereof. Glidants may be present in the composition from about 0.05 wt % to about 1 wt %, about 0.05 wt % to about 0.9 wt %, about 0.05 wt % to about 0.8 wt %, about 0.05 wt % to about 0.5 wt %, or about 0.05 wt % to about 0.1 wt % of the total weight of the composition, or any value between these ranges.

In some examples, pharmaceutical compositions can be a tablet and further comprise a topcoat, such as, but not limited to, hydroxypropyl-methylcellulose coating or polyvinyl alcohol coating, and are available under the trade name Opadry, such as Opadry White, Opadry II (Opadry is a registered trademark of BPSI Holdings LLC, Wilmington, Del., USA). Topcoats may be present in the composition from about 1 wt % to about 10 wt %, about 1 wt % to about 9 wt %, about 1 wt % to about 8 wt %, about 1 wt % to about 7 wt %, about 1 wt % to about 6 wt %, or about 1 wt % to about 5 wt % of the total weight of the composition, or any value between these ranges.

In some examples, pharmaceutical compositions can further comprise one or more preservative agents. Examples of preservative agents include but are not limited to sodium benzoate, paraoxybenzoic acid esters, methyl, ethyl, butyl, and propyl parabens, chlorobutanol, benzyl alcohol, phenylethylalcohol, dehydroacetic acid, sorbic acid, benzalkonium chloride (BKC), benzethonium chloride, phenol, phenylmercuric nitrate, thimerosal, or combinations thereof. Preservative agents can be included in the liquid dosage form. The preservative agents can be in an amount sufficient to extend the shelf-life or storage stability, or both, of the liquid dosage form. Preservatives may be present in the composition from about 0.05 wt % to about 1 wt %, about 0.05 wt % to about 0.9 wt %, about 0.05 wt % to about 0.8 wt %, about 0.05 wt % to about 0.5 wt %, or about 0.05 wt % to about 0.1 wt % of the total weight of the composition, or any value between these ranges.

In some examples, pharmaceutical compositions can further comprise one or more flavoring agents. Examples of flavoring agents include but are not limited to synthetic flavor oils and flavoring aromatics and/or natural oils, extracts from plants leaves, flowers, fruits, and so forth and the like or any combinations thereof. Additional examples include cinnamon oil, oil of wintergreen, peppermint oils, clove oil, bay oil, anise oil, eucalyptus, thyme oil, cedar leaf oil, oil of nutmeg, oil of sage, oil of bitter almonds, and cassia oil and the like or any combinations thereof. Also useful as flavors are vanilla, citrus oil, including lemon, orange, grape, lime and grapefruit, and fruit essences, including apple, banana, pear, peach, strawberry, raspberry, cherry, plum, pineapple, apricot, strawberry flavor, tutti-fruity flavor, mint flavor, or any combinations thereof. Flavoring agents may be present in the composition from about 0.1 wt % to about 5 wt %, about 0.1 wt % to about 4 wt %, about 0.1 wt % to about 3 wt %, about 0.1 wt % to about 2 wt %, or about 0.1 wt % to about 1 wt % of the total weight of the composition, or any value between these ranges.

The pharmaceutical compositions can generally be in any physical form suitable for use in treating a subject. These forms can be referred to as a unit dosage form, such as an individual pill or tablet. In some examples, the pharmaceutical compositions can be formulated as tablets, capsules, granules, powders, liquids, suspensions, gels, syrups, slurries, suppositories, patches, nasal sprays, aerosols, injectables, implantable sustained-release formulations, or mucoadherent films. In some examples, the pharmaceutical compositions may be formed as a tablet, a bi-layer tablet, a capsule, a multiparticulate, a drug coated sphere, a matrix tablet, or a multicore tablet. A physical form can be selected according to the desired method of treatment.

The pharmaceutical compositions can be manufactured by various conventional methods such as conventional mixing, dissolving, granulating, dragee-making, levigating, emulsifying, encapsulating, entrapping, or lyophilizing processes. Pharmaceutical compositions can be formulated in a conventional manner using one or more physiologically acceptable carriers, diluents, excipients or auxiliaries that facilitate processing of the active agent into preparations that can be used pharmaceutically. Proper formulation can be selected upon the route of administration chosen.

When the above-described composition is in powder form, it can be used conveniently to prepare beverage, paste, jelly, capsules, or tablets. Lactose and corn starch are commonly used as diluents for capsules and as carriers for tablets. Lubricating agents, such as magnesium stearate, are typically included in tablets.

The compositions of this invention can be a dietary supplement or a pharmaceutical formulation. As a dietary supplement, additional nutrients, such as minerals or amino acids may be included. The composition can also be a food product. As used herein, the term "food" broadly refers to any kinds of liquid and solid/semi-solid materials that are used for nourishing humans and animals, for sustaining normal or accelerated growth, or for maintaining stamina or alertness. Examples of human food products include, but are not limited to, tea-based beverages, juice, coffee, milk, jelly, cookies, cereals, chocolates, snack bars, herbal extracts, dairy products (e.g., ice cream, and yogurt), soybean product (e.g., tofu), and rice products.

Method of Treating Amyotrophic Lateral Sclerosis

In some embodiments, a method of treating amyotrophic lateral sclerosis (ALS), wherein the method comprises administering to a patient in need thereof a therapeutically effective amount of quercetin, vitamin B3, vitamin C, zafirlukast and optionally folic acid. In some embodiments, a method of treating ALS, wherein the method comprises administering to a patient in need thereof a therapeutically effective amount of quercetin, vitamin B3, vitamin C, a thiol isomerase inhibitor, and optionally folic acid, wherein the extracellular thiol isomerase inhibitor is zafirlukast, montelukast, CGP-13501, CGP-7930, alosetron, balsalazide, benserazide, butaclamol, leva-dopa, mesalazine, oxcarbazepine, a pharmaceutically acceptable salt, prodrug, and/or a solid state form thereof.

Diagnosis of ALS is based on clinical signs, established by a neurologist on the basis of history, topographic distribution of the neuronal loss and the finding of some characteristic cytological changes. Use of the described methods and pharmaceutical compositions can result in a slowing, reduction or elimination of disease, symptom, or other undesired property in a subject relative to a control population (for example, without treatment by the described methods and materials). Use of the described methods and pharmaceutical compositions can result in cessation or slowing down in the progression of the disease, symptom, or other undesired property in a subject relative to a control population. Mast cell dysregulation has been linked with the pathophysiology of ALS. Use of the described methods and pharmaceutical compositions can result in a down regulation of mast cell-induced IL-17, Tryptase, Substance P, and histamine. This in turn can result in an improvement in lung function and prevent loss of the ability to fully inflate the lungs. The reduction can generally be reduced by any amount. For example, the reduction can be at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, at least about 99%, and in an ideal situation, about 100% reduction (complete elimination of disease, symptom, or other undesired property).

In some embodiments, a method of treating ALS comprises inhibiting or preventing cytokine production in a patient, the method comprising administering a therapeutically effective amount of quercetin, vitamin B3, vitamin C, zafirlukast and optionally folic acid. As sentinel cells that sense danger in the form of pathogens or other types of injury at the onset of inflammation, mast cells play a pivotal role in initiating and propagating immune responses. Dysregulated mast cell function has been critically implicated in the pathology of ALS. In an embodiment, a method of inhibiting or preventing cytokine production in a patient, the method comprises administering a therapeutically effective amount quercetin, vitamin B3, vitamin C, zafirlukast, and optionally folic acid. to a patient in need thereof. In some embodiments, therapeutically effective amount quercetin, vitamin B3, vitamin C, zafirlukast, and optionally folic acid can reduce or slow the onset of muscle weakness, loss of lung function due to loss of chest expansion ability.

In some embodiments, a method of treating amyotrophic lateral sclerosis (ALS), wherein the method comprises administering to a patient or subject in need thereof a therapeutically effective amount of quercetin, vitamin B3, vitamin C, zafirlukast, and optionally folic acid, wherein the method of treating results in at least one of the following: reduction in neuroinflammation in a degenerating spinal cord, reduction in the number of reactive astrocytes, reduction in the number of hypertrophic astrocytes in the lumbar spinal cord, reduction in microgliosis, and reduction in the number of ventral horn motor neurons expressing misfolded SOD1 and ubiquitin, and a reduction in the markers of mast cell activity, reduction or slowing of the onset of muscle weakness, loss of lung function due to loss of chest expansion ability.

The method of this invention significantly lowers cholesterol and levels, and increases the hemoglobin levels, the number of reticulocytes, and the mass of red blood cells and may also reduce the markers of mast cell activity. Further, this composition results in increased mitochondrial biogenesis or retention (e.g., in muscle and brain cells), reduced mitochondrial DNA damage and loss of mitochondria, or increased cytochrome C levels and citrate synthase activities. Thus, it is useful in treating disease associated with mitochondrial deficiencies in both humans and animals. This composition can also induce gene expression and activity of T-helper lymphocyte (Th-1) cytokines (e.g., interferon gamma) and can down-regulate T-helper lymphocyte 2 (Th-2) cytokines (e.g., interleukin 13). In addition, it can inhibit the expression and/or activity of one or more of the following three enzymes: matrix metalloproteinase 1 (MMP1), matrix metalloproteinase 2 (MMP2), and cyclooxygenase 2 (COX2). It can also block pathways mediated by epidermal growth factor receptor, such as epiregulin-mediated pathways. This composition can be used to prevent neurodegeneration by chelating excess iron accumulation in neurons. It also can be an activator of Sirtuin and can increase mitochondrial size, efficiency and production with SIRT 1, 2, 3, 4, PGC1 alpha, Citrate Synthase and Cytochrome C all showing increased expression.

This method can also be used for treating diseases or disorders, such as a, a neurological or neurodegenerative disease (e.g., dyslexia, dyspraxia, autism, Asperger's disease, Alzheimer's disease, mild cognitive impairment, and Huntington's disease,).

Further, this method can be used to treat certain symptoms of the above-mentioned diseases or disorders. For example, it can be used to lessen certain symptoms of ALS, including muscle weakness, specifically weakness in legs, feet, or ankles, difficulty walking or performing daily activities, wasting of muscles, pain (such as facial pain or pain without apparent cause), muscle cramps, twitching in arms, shoulders, or tongue, electrical shock sensation, loss of awareness of location of body parts, loss of coordination (such as in speech), slurred speech, trouble swallowing, increased frequency of falls, loss of posture, shaking when performing fine movements, loss of ability to produce rapidly alternating movement (e.g., movement in a rhythm), and short-term or long term memory loss. This method can be used to improve lung function and chest expansion in ALS patients. In addition, this method can also be used as a dietary supplement to improve the quality of life of a patient.

The method described above can be preliminarily screened for efficacy in treating the above-described conditions by in vitro assays and then confirmed by animal experiments and clinic trials. Other suitable analytical and biological assays are apparent to those of ordinary skill in the art. For example, the bioavailability of quercetin can be measured by conducting pharmacokinetic studies and evaluated by the area under the curve in a plasma-drug concentration time curve.

The compounds and pharmaceutical compositions described herein may be administered at therapeutically effective dosage levels to treat the recited conditions, disorders, and diseases.

The compounds and pharmaceutical compositions described herein may be administered at prophylactically effective dosage levels to mitigate or prevent the recited conditions, disorders, and diseases.

The administration can be conducted daily for several days (for example about 2 to about 7 days), for several weeks (for example about 1 to about 4 weeks, specifically about 2 or about 3 weeks), or for several months (for example about 1 to about 36 months, specifically about 2 to about 24 months, and yet more specifically about 6 to about 12 months). In some embodiments, administration can be conducted daily for the remainder of the patient's life.

A therapeutically effective amount may range from about 0.001 pg/kg/day to about 500 mg/kg/day, preferably 0.01 pg/kg/day and 100 mg/kg/day. The skilled artisan will appreciate that certain factors may influence the dosage required to effectively treat a patient, including but not limited to the severity of the disease or disorder, previous treatments, the general health and/or age of the patient, and other diseases present. Moreover, treatment of a patient with a therapeutically effective amount of the compound can include a single treatment or, can include a series of treatments. It will also be appreciated that the effective dosage of a compound used for treatment may increase or decrease over the course of a particular treatment.

The method of administering an effective amount of quercetin, vitamin B3, vitamin C, zafirlukast and optionally folic acid, can occur once, twice, or three times a day, or more, to the patient in need thereof. Within this embodiment, the administration can be made orally.

Administration may be performed by generally any method. Methods of administering include infusion or injection of the composition. Example delivery methods of administering include topical delivery, subcutaneous delivery, intravenous injection (IV) delivery, intramuscular injection (IM) delivery, intrathecal injection (IT) delivery, intraperitoneal injection (IP) delivery, transdermal delivery, subcutaneous delivery, oral delivery, transmucosal oral delivery, pulmonary delivery, inhalation delivery, intranasal delivery, buccal delivery, rectal delivery, vaginal delivery, and combinations thereof. In some embodiments, the administering comprises oral delivery.

For injection, pharmaceutical compositions can be formulated in aqueous solutions, preferably in physiologically compatible buffers such as Hanks solution, Ringer's solution, or physiological saline buffer and/or in certain emulsion formulations. Solutions can contain one or more formulatory agents such as suspending, stabilizing and/or dispersing agents. In certain examples the pharmaceutical compositions can be provided in powder form for constitution with a suitable vehicle, for example, sterile pyrogen-free water, before use. For transmucosal administration, one or more penetrants appropriate to the barrier to be permeated can be used in the formulation. Such penetrants are generally known in the art.

For oral administration the composition may be formulated as tablets, pills, dragees, capsules, liquids, gels, syrups, slurries, suspensions and the like, for oral ingestion by a patient to be treated. For oral solid formulations such as, for example, the compositions may take the form of powders, capsules and tablets. For buccal administration, the compositions may take the form of tablets, lozenges, etc. formulated in conventional manner.

For administration by inhalation, the pharmaceutical composition can be delivered in the form of an aerosol spray from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the compound and a suitable powder base such as lactose or starch.

The subject can generally be any mammal. Examples of subjects include a primate, a human, a dog, a cat, a mouse, a rat, a cow, a horse, a pig, a rabbit, and a ferret. In some examples, the subject is a human. The terms "subject", "individual", or "patient" are used interchangeably and as used herein are intended to include human and non-human animals. Non-human animals include all vertebrates, for example, mammals and non-mammals, such as non-human primates, sheep, dogs, rats, cats, cows, horses, ferrets, chickens, amphibians, and reptiles. Examples of mammals include non-human primates, sheep, dogs, cats, cows, ferrets, and horses.

EXAMPLES

Example 1: Evidence for a Neuroprotective Effect Post-Paralysis Treatment with Isoquercetin in an ALS Murine Model Amyotrophic lateral sclerosis (ALS) is a paralytic neurodegenerative disease characterized by the progressive degeneration of upper and lower motor neurons. Survival after diagnosis varies between 1 and 5 years or more, largely determined on the rate of spread of motor neuron pathology. Paralysis progression in rodent models of ALS appears to be modulated, at least in part, by glial cells that become reactive, proliferate, and express inflammatory mediators in the degenerating spinal cord (Barbeito, et al., 2004; Ilieva et al., 2009; Lobsiger, et al., 2007). The SOD1G93A mutant rat model of ALS, has been well characterized as a model of the disease (Howland, et al., 2002). The model is characterized by a rapid spread of paralysis after the paralysis onset, which is associated with marked glial cell activation and the emergence of aberrant glial cells that actively proliferate around degenerating motor neurons (Howland, et al., 2002; Diaz, et al., 2011). Furthermore, aberrant glial cells display a marked neurotoxic potential on cultured motor neurons (Diaz, et al., 2011; Trias, et al., 2013), suggesting that they might directly contribute to the rapid spread of paralysis of ALS rats.

Pharmacologically downregulation of aberrant glial cells and reactive microglia by the tyrosine kinase inhibitor, masitinib, results in slowed paralysis progression in the rat model of ALS (Trias, et al., 2016). We have theorized that microglia activation in the ALS spinal cord could be sensitive to the quercetin derivative, isoquercetin), orally administered to SOD1G93A rats, together with vitamin C and niacin. Quercetin is a naturally occurring flavonol characterized by a phenyl benzo(y)pyrone-derived structure, with strong antioxidant, neuroprotective, and immunomodulatory effects. While the bio-availability of quercetin is sometimes limited, its derivate isoquercetin (quercetin-3-O-β-d-glucopyranoside), has an improved pharmacokinetic profile and is efficiently converted in vivo into quercetin (Stopa, et al., 2017). Several reports have shown evidence for the neuroprotective effects of quercetin in Alzheimer's disease and ALS (Lazo-Gomez and Tapia, 2017) animal models (Jung, et al., 2010; Sabogal-Guáqueta, et al., 2015).

Materials and Methods: Animals: Male SOD1G93A progeny were used for further breeding to maintain the line. Rats were housed in a centralized animal facility with a 12-h light-dark cycle with ad libitum access to food and water. Perfusion with fixatives was performed under 90% ketamine-10% xylazine anesthesia and all efforts were made to minimize animal suffering, discomfort, or stress. All procedures using laboratory animals were performed in accordance with the national and international guidelines and were approved by the Institutional Animal Committee for animal experimentation. Male hemizygous NTac:SD-TgN (SOD1-G93A)L26H rats (Taconic), originally developed by Howland et al. (2002), were bred locally by crossing with wild-type nontransgenic Sprague-Dawley female rats.

Treatment with Isoquercetin: All rats were weighed and evaluated for motor activity daily. Disease onset was determined for each animal when pronounced muscle atrophy was accompanied by abnormal gait, typically expressed as subtle dragging of one hind limb. End-stage was defined by a lack of righting reflexes or the inability to reach food and water.

Immunohistochemical staining of rat spinal cords: After 15 days of treatment using 30 mg/kg/day of isoquercetin, starting after paralysis onset, animals were deeply anesthetized and transcardial perfusion was performed with 0.9% saline and 4% paraformaldehyde in 0.1 M PBS (pH 7.2-7.4). Fixed spinal cords were removed, postfixed by immersion for 24 h, and then transverse sectioned (30 pin) in a Leica cryostat. Serial sections were collected in 100 mM PBS for immunohistochemistry. Free-floating sections were permeabilized for 30 min at room temperature with 0.3% Triton X-100 in PBS, passed through washing buffered solutions, blocked with 5% BSA:PBS for 1 h at room temperature, and incubated overnight at 4° C. in a solution of 0.3% Triton X-100 and PBS containing the primary antibodies, rabbit anti-GFAP (1:500, Sigma), mouse anti-S100β (1:400, Sigma), rabbit anti-Iba1 (1:300, abcam), mouse anti-CD68 (1:200, abcam), mouse anti-ChAT (choline acetyltransferase) (1:300, Millipore). After washing, sections were incubated in 1:1000-diluted secondary antibodies conjugated to Alexa Fluor 488 and/or Alexa Fluor 633 (1:1000, Invitrogen). Antibodies were detected by confocal microscopy using a confocal ZEISS LSM 780.

Figure 1:
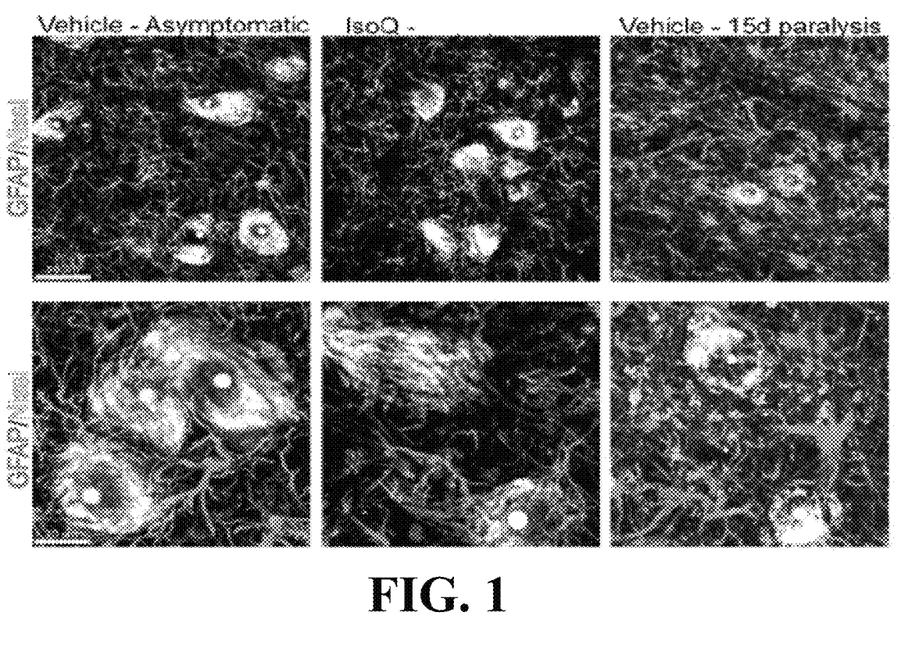
FIG. 1 depicts an exemplary evaluation of isoquercetin amelioration of astrocytosis. Confocal images from spinal cord sections stained with GFAP and Nissl staining. Note the significant reduction of astrocytes surrounding motor neurons (in white) in isoquercetin-treated rat spinal cords when compared with vehicle-treated ones. Scale bar 5 and 20 μm.

Results: Post-paralysis isoquercetin treatment reduces neuroinflammation in the degenerating spinal cord. We explored whether postparalysis treatment with isoquercetin could reduce the number of reactive astrocytes in the degenerating spinal cord, which were identifiable as large GFAP-positive cells located around motor neurons as described previously. Rats were orally treated with isoquercetin (30 mg/kg/day), starting right after paralysis onset and during the next 15 days, As compared with rats treated with vehicle, isoquercetin (IsoQ) significantly reduced the number of hypertrophic astrocytes in the lumbar spinal cord (FIG. 1; scale bar 5 and 20 pin).

Figure 2:
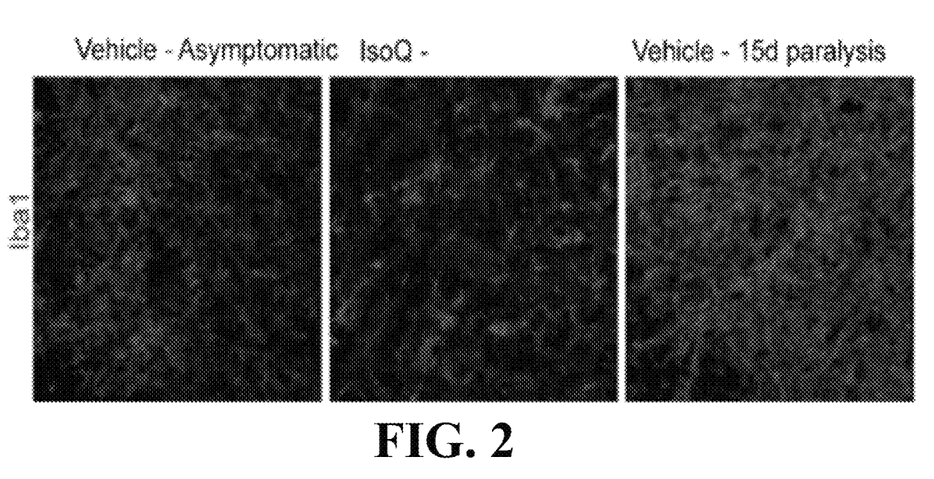
FIG. 2 depicts an exemplary evaluation of isoquercetin amelioration of microgliosis. Confocal images of microglia marker Iba1. Significant reduction of microglial cells in isoquercetin-treated rat spinal cords when compared with vehicle-treated ones.

Post-paralysis isoquercetin treatment significantly reduced microgliosis. We assessed microgliosis by assessing the number of cells expressing Iba1+ cells in the ventral horn of the lumbar spinal cord, when compared with vehicle-treated animals. Notably, there was a reduction of hypertrophic Iba1+ microglia cells surrounding motor neurons (FIG. 2).

Figure 3:
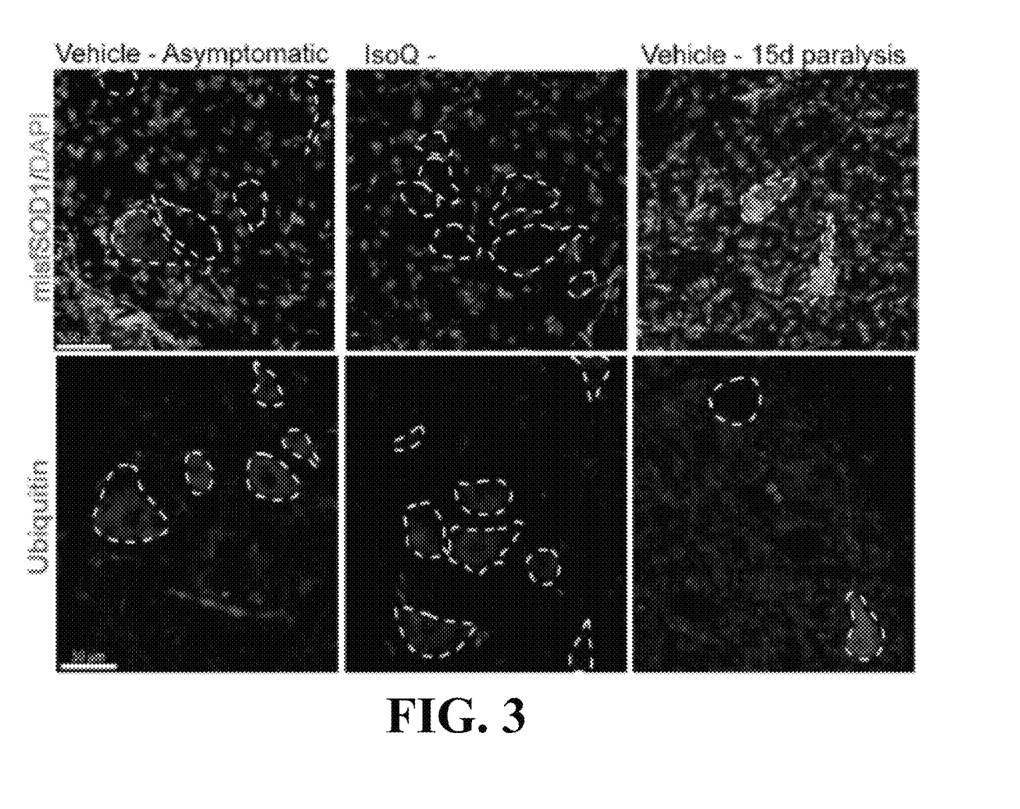
FIG. 3 depicts an exemplary evaluation of isoquercetin amelioration of motor neuron pathology. Confocal images of spinal motor neurons stained with antibodies against misfolded SOD1 and Ubiquitin. Note the significant reduction of both markers in isoquercetin treated rat spinal cords when compared with vehicle-treated ones.

Isoquercetin ameliorates motor neuron pathology. Because motor neuron death is the main pathological feature of symptomatic rodent models and human ALS, we used the same experimental setting to determine if motor neuron pathology was influenced by isoquercetin treatment. As shown in FIG. 3, in vehicle-treated SOD1G93A rats, the number of ventral horn motor neurons expressing misfolded SOD1 and Ubiquitin were apparently reduced by isoquercetin treatment when measured 15 days after paralysis onset, as compared with vehicle-treated rats. Misfolded SOD1 and Ubiquitin are considered reliable markers of motor neuron pathology in ALS (Light, et al., 1991).

Isoquercetin is a well-established class of flavonoid having multifaceted antioxidants, anti-inflammatory and neuroprotective effects (Lazo-Gomez and Tapia, 2017; Jung, et al., 2010; Sabogal-Guáqueta, et al., 2015). Here, we show evidence that isoquercetin therapeutically modulates the neuroinflammation associated with the ALS progression. Notably, treatment of already paralytic rats with isoquercetin resulted in an apparent decrease in astrocytosis and microgliosis in the degenerating spinal cord. Such a therapeutic approach is appealing in the clinical setting of ALS where drug treatment is initiated only after overt motor symptoms.

Example 2: Evidence for a Synergistic Neuroprotective Effect of Post-Paralysis Treatment with Isoquercetin and Zafirulkast in an ALS Murine Model Materials and Methods: Treatment with isoquercetin and zafirlukast: Disease onset is determined for each animal when pronounced muscle atrophy is accompanied by abnormal gait, typically expressed as subtle dragging of one hind limb. End-stage is defined by a lack of righting reflexes or the inability to reach food and water.

Immunohistochemical staining of rat spinal cords: After 15 days of treatment using a composition comprising isoquercetin, vitamin B3, vitamin C, zafirlukast, and optionally folic acid, spinal cords from animals are removed and prepared for immunohistochemistry as is described in Example 1. Primary antibodies include rabbit anti-GFAP (1:500, Sigma), mouse anti-S100β (1:400, Sigma), rabbit anti-Iba1 (1:300, abcam), mouse anti-CD68 (1:200, abcam), mouse anti-ChAT (choline acetyltransferase) (1:300, Millipore). After washing, sections are incubated in 1:1000-diluted secondary antibodies conjugated to Alexa Fluor 488 and/or Alexa Fluor 633 (1:1000, Invitrogen). Antibodies are detected by confocal microscopy using a confocal ZEISS LSM 780.

Results: Treatment with a composition comprising isoquercetin, vitamin B3, vitamin C, zafirlukast and optionally folic acid has a synergistic effect of reducing mast cell activation and neuroinflammation more than with isoquercetin or zafirlukast alone. Reducing mast cell activation can result in inhibition or down-regulation of IL-17, tryptase, substance P, and histamine. Post-paralysis treatment with the composition reduces neuroinflammation in the degenerating spinal cord measured by a reduction in the number of reactive astrocytes in the degenerating spinal cord, which are identifiable as large GFAP-positive cells located around motor neurons. Treatment with the composition also reduced the number of hypertrophic astrocytes in the lumbar spinal cord. Post-paralysis treatment with the composition significantly reduced microgliosis measured by the number of cells expressing Iba1+ cells in the ventral horn of the lumbar spinal cord. isoquercetin ameliorates motor neuron pathology. Motor neuron pathology is influenced by treatment with the composition as measured by a reduction in the number of ventral horn motor neurons expressing misfolded SOD1 and Ubiquitin 15 days after paralysis onset, as compared with vehicle-treated rats.

What is claimed is:

1. A method of treating amyotrophic lateral sclerosis (ALS), the method comprising administering to a subject in need thereof an effective amount of a first pharmaceutical composition comprising isoquercetin, vitamin B3, vitamin C, and a second pharmaceutical composition comprising zafirlukast.

2. The method of claim 1, wherein the first pharmaceutical composition comprises about 250 mg to about 2500 mg of isoquercetin.

3. The method of claim 1, wherein the first pharmaceutical composition comprises about 20 µg to about 3 g of vitamin B3.

4. The method of claim 1, wherein the first pharmaceutical composition comprises about 200 µg to about 3 g of vitamin C.

5. The method of claim 1, wherein the first pharmaceutical composition further comprises folic acid.

6. The method of claim 5, wherein the first pharmaceutical composition comprises about 1000 µg to about 3000 µg of folic acid.

7. The method of claim 1, wherein the second pharmaceutical composition comprises about 5 mg to about 30 mg of zafirlukast.

8. The method of claim 1, wherein the effective amount is sufficient to slow or halt progression of one or more of the symptoms of ALS.

9. The method of claim 3, wherein the first pharmaceutical composition comprises about 20 µg to about 250 mg of vitamin B3.

10. The method of claim 4, wherein the first pharmaceutical composition comprises about 50 mg to 2.5 g of vitamin C.

11. The method of claim 1, wherein IL-17 is downregulated.

12. The method of claim 8, wherein the one or more of the symptoms of ALS are selected from the group consisting of muscle weakness, difficulty walking, difficulty performing daily activities, wasting of muscles, pain, muscle cramps, twitching, loss of awareness of location of body parts, loss of coordination, slurred speech, trouble swallowing, thrombosis, increased frequency of falls, loss of posture, shaking when performing fine movements, loss of ability to produce rapidly alternating movement, loss of lung function, loss of the ability to fully inflate the lungs, and loss of chest expansion.

13. The method of claim 1, wherein the administering results in reduced misfolded SOD1, reduced misfolded ubiquitin, decreased astrocytosis, decreased microgliosis, or a combination thereof.

* * * * *